US007214845B2

(12) United States Patent
Randolph et al.

(10) Patent No.: US 7,214,845 B2
(45) Date of Patent: May 8, 2007

(54) DISPROPORTIONATION OF HYDROCARBONS

(75) Inventors: Bruce B. Randolph, Bartlesville, OK (US); Marvin M. Johnson, Bartlesville, OK (US); Edward L. Sughrue, II, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 68 days.

(21) Appl. No.: 11/049,250

(22) Filed: Feb. 2, 2005

(65) Prior Publication Data

US 2005/0131264 A1    Jun. 16, 2005

Related U.S. Application Data

(63) Continuation of application No. 10/317,567, filed on Dec. 12, 2002, now abandoned.

(51) Int. Cl.
 *C07C 6/08* (2006.01)
(52) U.S. Cl. ..................................................... 585/708
(58) Field of Classification Search ................ 585/708
 See application file for complete search history.

(56) References Cited

U.S. PATENT DOCUMENTS

| | | | |
|---|---|---|---|
| 3,676,522 A | * | 7/1972 | Sieg ........................ 585/303 |
| 3,914,330 A | * | 10/1975 | Hughes ...................... 208/138 |
| 4,665,272 A | | 5/1987 | Bakas et al. |
| 4,665,273 A | | 5/1987 | Johnson et al. |
| 4,754,100 A | | 6/1988 | Sorensen et al. |
| 4,834,867 A | | 5/1989 | Gilson |
| 4,929,337 A | | 5/1990 | Herbst et al. |
| 5,055,176 A | | 10/1991 | Herbst et al. |
| 5,171,912 A | | 12/1992 | Harandi |
| 5,326,925 A | | 7/1994 | Sachtler |
| 5,414,184 A | | 5/1995 | Wu et al. |
| 5,489,727 A | | 2/1996 | Randolph et al. |
| 5,557,029 A | | 9/1996 | Lin et al. |
| 5,648,590 A | | 7/1997 | Hsu et al. |
| 5,763,727 A | | 6/1998 | Collins et al. |
| 5,831,139 A | | 11/1998 | Schmidt et al. |
| 6,018,088 A | | 1/2000 | Olah |
| 6,124,516 A | | 9/2000 | Wu et al. |
| 6,140,547 A | | 10/2000 | Lin et al. |
| 6,423,880 B1 | * | 7/2002 | Randolph et al. ........... 585/708 |

* cited by examiner

*Primary Examiner*—Thuan D. Dang
(74) *Attorney, Agent, or Firm*—Bronwyn A. Welvaert

(57) ABSTRACT

A novel hydrocarbon disproportionation process is provided and includes contacting a hydrocarbon feed comprising at least one paraffin with a disproportionation catalyst comprising a support component, a metal, and a halogen in a disproportionation reaction zone under disproportionation reaction conditions.

14 Claims, No Drawings

DISPROPORTIONATION OF HYDROCARBONS

This Application is a Continuation of application Ser. No. 10/317,567, filed on Dec. 12, 2002, now abandoned.

BACKGROUND OF THE INVENTION

This invention relates to the disproportionation of hydrocarbons. More particularly, this invention relates to the disproportionation of paraffins in the presence of an isomerization catalyst.

The disproportionation of hydrocarbons is well known in the art. This process has gained importance due to governmental regulations requiring reduction of the amount of volatile $C_4$ and $C_5$ alkanes present in gasoline. Also, there is an incentive to convert isopentanes, for example, to higher isoparaffins, such as, isohexane which is a lower vapor pressure motor fuel component, and to isobutane which is a feedstock for alkylation with olefins to high octane alkylate and also for the production of MTBE.

Therefore, development of an improved process for disproportionating hydrocarbons would be a significant contribution to the art.

SUMMARY OF THE INVENTION

It is an object of the present invention to provide an improved process for disproportionating hydrocarbons.

It is another object of the present invention to provide an improved process for disproportionating hydrocarbons by contacting a hydrocarbon feedstock with a catalyst comprising a metal, a halogen, and a support component.

In accordance with the present invention, a process for disproportionating hydrocarbons has been discovered comprising contacting a hydrocarbon feed comprising at least one paraffin with a catalyst comprising a support component, a metal, and a halogen in a disproportionation reaction zone under disproportionation reaction conditions.

Other objects and advantages will become apparent from the detailed description and the appended claims.

DETAILED DESCRIPTION OF THE INVENTION

The process of the present invention comprises, consists of, or consists essentially of contacting a hydrocarbon feed comprising at least one paraffin with a catalyst comprising
(a) a support component,
(b) a metal selected from the group consisting of platinum, palladium, iron, cobalt, nickel, zinc, ruthenium, rhodium, osmium, iridium, and combinations of any two or more thereof, and
(c) a halogen in a disproportionation reaction zone under disproportionation reaction conditions.

The hydrocarbon feed can be any hydrocarbon-containing feed which comprises, consists of, or consists essentially of at least one paraffin. Preferably, the feed comprises at least one $C_4$ or $C_5$ paraffin including, but not limited to, normal butane, normal pentane, and isopentane. Most preferably, the feed comprises at least one isopentane.

The hydrocarbon feed can be a stream obtained from an alkylation process, or obtained from the processing of natural gas liquids, or a stream obtained from a thermal or catalytic cracking process.

The catalyst used in the inventive process can comprise, consist of, or consist essentially of (a) a support component, (b) a metal selected from the group consisting of platinum, palladium, iron, cobalt, nickel, zinc, ruthenium, rhodium, osmium, iridium, and combinations of any two or more thereof, and (c) a halogen. Preferably, the halogen is selected from the group consisting of chlorine, bromine, and combinations thereof, and the metal is selected from the group consisting of platinum, palladium, and combinations thereof, and the support component is selected from the group consisting of alumina, silica-alumina, a zeolite, zirconia, a borate, an aluminum borate, and combinations thereof. Most preferably, the support component comprises alumina, the metal comprises platinum, and the halogen comprises chlorine.

The process of this invention preferably employs an initiator, which is added to the hydrocarbon feed. The initiator is selected from the group consisting of a chloroalkane, a branched paraffin, at least one olefin, and combinations thereof. Preferably, the initiator comprises at least one olefin.

The initiator useful in the present invention can be any compound capable of initiating a hydrogen transfer reaction. The chloroalkane preferably comprises a compound selected from the group consisting of chloropropane, chlorobutanes, chloropentanes, and combinations of any two or more thereof. The branched paraffin preferably comprises a multi-branched paraffin having a different molecular weight than the primary component in the hydrocarbon feed. The at least one olefin preferably has in the range of from 2 to 20 carbon atoms per molecule, and combinations of any two or more thereof. More preferably, the at least one olefin has in the range of from 3 to 8 carbon atoms per molecule. Most preferably, the at least one olefin has in the range of from 5 to 6 carbon atoms per molecule.

When present, the concentration of the initiator in the disproportionation reaction zone, based on the combined weight of the hydrocarbon feed and initiator in the disproportionation reaction zone, is at least about 0.01 weight percent, preferably at least about 0.1 weight percent and most preferably at least 0.9 weight percent.

In another embodiment of the invention, the catalyst comprises, consists of, or consists essentially of a) a support component, b) a metal selected from the group consisting of platinum, palladium, iron, cobalt, nickel, zinc, ruthenium, rhodium, osmium, iridium, and combinations of any two or more thereof, c) a halogen and d) an element selected from the group consisting of boron, gallium, indium, thallium, and combinations of any two or more thereof. Preferably, the element is gallium.

The disproportionation reaction takes place in a disproportionation reaction zone. The disproportionation reaction zone can be any reactor system known to those skilled in the art to be suitable for use in disproportionating hydrocarbons in the presence of a catalyst. Typical reactor systems useful in the present invention include, but are not limited to, batch type operations, a fixed bed system, a moving bed system, and a fluidized bed system.

The disproportionation reaction conditions can be any conditions suitable for disproportionating hydrocarbons. Preferably, the disproportionation reaction conditions include a temperature in the range of from about 75° F. to about 500° F., more preferably from about 100° F. to about 300° F., and most preferably from 200° F. to 300° F. Also, the disproportionation reaction conditions include a contact time of the hydrocarbon feed with the disproportionation catalyst in the range of from about 30 seconds to about 2 hours, preferably from about 5 minutes to about 1 hour, and most preferably from 20 minutes to 50 minutes, and, optionally, include the presence of the above described initiator.

The catalyst can be reactivated by being stripped with hydrogen.

The following examples demonstrate the advantages of the present invention. The examples are for illustration purposes only and are not intended to limit the invention as set out in the specification and the appended claims.

EXAMPLE I

A 20 mL sample of a catalyst containing 1.5% $Ga_2O_3$ on $Al_2O_3$ with 0.3% platinum was placed into a tubular reactor with an inert support above and below the catalyst. A nitrogen feed was set at 50 sccm and the temperature was set at 500° F. A 3.4 gram quantity of carbon tetrachloride was charged to the reactor at a rate of 0.1 mL/min. After this catalyst was chlorided, as described above, an isopentane feed was charged to the reactor at a feed rate of 42.4 mL/hr (LHSV=2 $hr^{-1}$). Initial temperature was set at 250° F. and a hydrogen co-feed was set at 2.5 sccm. Table I shows the results for five different samples taken approximately after 1 hour, 2 hours, 3 hours, 4.5 hours and 5.5 hours on stream, respectively.

The catalyst underwent hydrogen stripping for 65 hours at a hydrogen flow rate of 50 sccm with temperature set at 300° F. After reactivation, an isopentane feed was once again charged to the reactor at a feed rate of 42.4 mL/hr (LHSV=2 $hr^{-1}$). Initial temperature was set at 270° F. and a hydrogen co-feed was set at 2.5 sccm. Table II shows the results for 5 different samples taken approximately 1, 2, 3, 4 and 5 hours after reactivation, respectively.

TABLE II $iC_5$ Disproportionation Results from Platinum on Chlorided Alumina Catalyst with Gallium

| | | Time Since Reactivation, Hours | | | | |
|---|---|---|---|---|---|---|
| | Feed | 1 Hour | 2 Hours | 3 Hours | 4 Hours | 5 Hours |
| | | Product (wt %) | | | | |
| Propane | 0 | 0.058 | 0.010 | 0.005 | 0.003 | 0.006 |
| Isobutane | 0.053 | 9.389 | 4.350 | 2.754 | 1.946 | 2.378 |
| Butene | 0 | 0.002 | 0.001 | 0 | 0.001 | 0.001 |
| normal butane | 0.084 | 0.265 | 0.109 | 0.097 | 0.093 | 0.097 |

TABLE I $iC_5$ Disproportionation Results from Platinum on Chlorided Alumina Catalyst with Gallium

| | | Time On-Stream, Hours | | | | |
|---|---|---|---|---|---|---|
| | Feed | 1 Hour | 2 Hours | 3 Hours | 4.5 Hours | 5.5 Hours |
| | | Product (wt %) | | | | |
| propane | 0 | 0.089 | 0.007 | 0.004 | 0.002 | 0.001 |
| isobutane | 0.053 | 10.932 | 3.100 | 1.778 | 0.903 | 0.636 |
| butene | 0 | 0.002 | 0 | 0.001 | 0 | 0 |
| normal butane | 0.084 | 0.406 | 0.105 | 0.100 | 0.091 | 0.088 |
| neo-pentane | 0.193 | 0.209 | 0.19456 | 0.194 | 0.193 | 0.193 |
| isopentane | 99.235 | 78.384 | 91.126 | 94.155 | 96.690 | 97.444 |
| normal pentane | 0.414 | 1.580 | 0.892 | 0.757 | 0.652 | 0.634 |
| Unknown $C_1$–$C_5$ | 0.021 | 0.017 | 0.021 | 0.020 | 0.020 | 0.019 |
| 2,2-dimethylbutane | 0 | 0.254 | 0.042 | 0.035 | 0.02 | 0.010 |
| 2,3-dimethylbutane | 0 | 0.879 | 0.413 | 0.257 | 0.116 | 0.083 |
| 2-methylpentane | 0 | 3.602 | 2.026 | 1.354 | 0.663 | 0.475 |
| 3-methylpentane | 0 | 1.805 | 1.11 | 0.758 | 0.377 | 0.276 |
| normal hexane | 0 | 0.256 | 0.086 | 0.047 | 0.018 | 0.012 |
| Unknown $C_6$ | 0 | 0.004 | 0 | 0 | 0 | 0 |
| 2,2-dimethylpentane | 0 | 0.018 | 0.004 | 0.002 | 0.001 | 0 |
| 2,4-dimethylpentane | 0 | 0.182 | 0.074 | 0.044 | 0.016 | 0.008 |
| 2,2,3-trimethylbutane | 0 | 0.035 | 0.011 | 0.007 | 0.003 | 0.001 |
| 3,3-dimethylpentane | 0 | 0.037 | 0.038 | 0.007 | 0.010 | 0.003 |
| 2-methylhexane | 0 | 0.36 | 0.17 | 0.102 | 0.037 | 0.018 |
| 2,3-dimethylpentane | 0 | 0.115 | 0.055 | 0.033 | 0.012 | 0.006 |
| 3-methylhexane | 0 | 0.282 | 0.142 | 0.084 | 0.030 | 0.015 |
| 3-ethylpentane | 0 | 0.014 | 0.008 | 0.004 | 0.001 | 0 |
| 2,2,4-trimethylpentane | 0 | 0.003 | 0 | 0 | 0 | 0 |
| normal $C_7$ | 0 | 0.044 | 0.018 | 0.010 | 0.004 | 0.002 |
| Unknown $C_7$ | 0 | 0.023 | 0.008 | 0.006 | 0.004 | 0.002 |
| 2,2-dimethylhexane | 0 | 0.014 | 0.006 | 0.004 | 0.002 | 0.001 |
| 2,5-dimethylhexane | 0 | 0.038 | 0.017 | 0.011 | 0.005 | 0.002 |
| 2,4-dimethylhexane | 0 | 0.037 | 0.018 | 0.011 | 0.005 | 0.002 |
| 3,3-dimethylhexane | 0 | 0.004 | 0.001 | 0.001 | 0 | 0 |
| 2,3,4-trimethylpentane | 0 | 0.002 | 0 | 0 | 0 | 0 |
| 2,3,3-trimethylpentane | 0 | 0.001 | 0 | 0 | 0 | 0 |
| 2,3-dimethylhexane | 0 | 0.012 | 0.006 | 0.004 | 0.002 | 0 |
| 2-methylheptane | 0 | 0.044 | 0.023 | 0.015 | 0.006 | 0.002 |
| 4-methylheptane | 0 | 0.013 | 0.007 | 0.004 | 0.002 | 0 |
| 3,4-dimethylhexane | 0 | 0.004 | 0.002 | 0.001 | 0 | 0 |
| 3-methylheptane | 0 | 0.040 | 0.022 | 0.014 | 0.006 | 0.002 |
| Unknown $C_8$ | 0 | 0.001 | 0.001 | 0.001 | 0.001 | 0.001 |
| $C_9^+$ | 0 | 0.254 | 0.244 | 0.172 | 0.108 | 0.064 |

TABLE II-continued iC$_5$ Disproportionation Results from Platinum on Chlorided Alumina Catalyst with Gallium

| | | Time Since Reactivation, Hours | | | | |
|---|---|---|---|---|---|---|
| | Feed | 1 Hour | 2 Hours | 3 Hours | 4 Hours | 5 Hours |
| neo-pentane | 0.193 | 0.202 | 0.195 | 0.194 | 0.194 | 0.194 |
| Isopentane | 99.235 | 79.064 | 88.199 | 91.422 | 93.854 | 93.051 |
| normal pentane | 0.414 | 2.313 | 1.383 | 1.187 | 1.094 | 1.214 |
| Unknown C$_1$–C$_5$ | 0.021 | 0.020 | 0.022 | 0.022 | 0.024 | 0.021 |
| 2,2-dimethyl-butane | 0 | 0.178 | 0.066 | 0.036 | 0.021 | 0.044 |
| 2,3-dimethyl-butane | 0 | 0.098 | 0.594 | 0.433 | 0.277 | 0.324 |
| 2-methyl-pentane | 0 | 3.794 | 2.618 | 2.019 | 1.36 | 1.45 |
| 3-methyl-pentane | 0 | 2.083 | 1.456 | 1.129 | 0.767 | 0.809 |
| normal hexane | 0 | 0.339 | 0.163 | 0.104 | 0.060 | 0.092 |
| Unknown C$_6$ | 0 | 0.002 | 0 | 0 | 0 | 0 |
| 2,2-dimethyl-pentane | 0 | 0.014 | 0.005 | 0.003 | 0.001 | 0.002 |
| 2,4-dimethyl-pentane | 0 | 0.159 | 0.094 | 0.063 | 0.028 | 0.036 |
| 2,2,3-trimethyl-butane | 0 | 0.034 | 0.016 | 0.010 | 0.004 | 0.007 |
| 3,3-dimethyl-pentane | 0 | 0.020 | 0.009 | 0.006 | 0.002 | 0.004 |
| 2-methyl-hexane | 0 | 0.348 | 0.217 | 0.146 | 0.069 | 0.080 |
| 2,3-dimethyl-pentane | 0 | 0.124 | 0.074 | 0.049 | 0.022 | 0.028 |
| 3-methyl-hexane | 0 | 0.297 | 0.185 | 0.124 | 0.059 | 0.668 |
| 3-ethylpentane | 0 | 0.017 | 0.010 | 0.007 | 0.003 | 0.004 |
| 2,2,4-trimethyl-pentane | 0 | 0 | 0 | 0 | 0 | 0 |
| normal C$_7$ | 0 | 0.054 | 0.028 | 0.019 | 0.008 | 0.011 |
| Unknown C$_7$ | 0 | 0 | 0 | 0 | 0 | 0 |
| 2,2-dimethyl-hexane | 0 | 0.012 | 0.01 | 0.005 | 0.003 | 0.002 |
| 2,5-dimethyl-hexane | 0 | 0.024 | 0.016 | 0.011 | 0.005 | 0.004 |
| 2,4-dimethyl-hexane | 0 | 0.027 | 0.175 | 0.012 | 0.005 | 0.004 |
| 3,3-dimethyl-hexane | 0 | 0.002 | 0.002 | 0.001 | 0 | 0 |
| 2,3-dimethyl-hexane | 0 | 0.01 | 0.006 | 0.004 | 0.002 | 0.002 |
| 2-methyl-heptane | 0 | 0.033 | 0.022 | 0.016 | 0.007 | 0.006 |
| 4-methyl-heptane | 0 | 0.011 | 0.007 | 0.005 | 0.002 | 0.002 |
| 3,4-dimethyl-hexane | 0 | 0.004 | 0.002 | 0.002 | 0 | 0 |
| 3-methyl-heptane | 0 | 0.033 | 0.022 | 0.016 | 0.007 | 0.006 |
| Unknown C$_8$ | 0 | 0.002 | 0.001 | 0.001 | 0.001 | 0 |
| C$_9^+$ | 0 | 0.009 | 0.091 | 0.09 | 0.075 | 0.057 |

The catalyst was once again reactivated. After reactivation an isopentane feed was charged to the reactor at a feed rate of 21.2 mL/hr (LHSV=1 hr$^{-1}$). Initial temperature was set at 270° F. and a hydrogen co-feed was set at 2.5 sccm. Table III shows the results for five different samples taken approximately two hours, three hours, four hours, five hours, and six hours after reactivation, respectively.

TABLE III iC$_5$ Disproportionation Results from Platinum on Chlorided Alumina Catalyst with Gallium

| | | Time Since Reactivation, Hours | | | | |
|---|---|---|---|---|---|---|
| | Feed | 2 Hour | 3 Hours | 4 Hours | 5 Hours | 6 Hours |
| | | Product (wt %) | | | | |
| ethane | 0 | 0 | 0.008 | 0.001 | 0.001 | 0.002 |
| propane | 0 | 0.049 | 0.020 | 0.014 | 0.013 | 0.018 |
| isobutane | 0.053 | 9.501 | 7.692 | 6.262 | 6.127 | 6.967 |
| butene | 0 | 0.001 | 0.001 | 0.001 | 0.001 | 0.001 |
| normal butane | 0.084 | 0.225 | 0.131 | 0.118 | 0.117 | 0.125 |
| neo-pentane | 0.193 | 0.201 | 0.193 | 0.194 | 0.194 | 0.194 |
| isopentane | 99.235 | 77.846 | 79.659 | 82.890 | 83.390 | 81.726 |
| normal pentane | 0.414 | 2.243 | 1.975 | 1.748 | 1.728 | 1.697 |
| Unknown C$_1$–C$_5$ | 0.021 | 0.015 | 0.021 | 0.024 | 0.026 | 0.028 |
| 2,2-dimethyl-butane | 0 | 0.149 | 0.101 | 0.073 | 0.071 | 0.086 |
| 2,3-dimethyl-butane | 0 | 1.148 | 1.179 | 0.991 | 0.945 | 1.031 |
| 2-methyl-pentane | 0 | 4.346 | 4.593 | 4.012 | 3.895 | 4.204 |
| 3-methyl-pentane | 0 | 2.385 | 2.525 | 2.195 | 2.128 | 2.289 |
| normal hexane | 0 | 0.349 | 0.303 | 0.229 | 0.217 | 0.248 |
| Unknown C$_6$ | 0 | 0.004 | 0.002 | 0 | 0.002 | 0.002 |
| 2,2-dimethyl-pentane | 0 | 0.013 | 0.007 | 0.005 | 0.004 | 0.006 |
| 2,4-dimethyl-pentane | 0 | 0.18 | 0.190 | 0.146 | 0.132 | 0.161 |
| 2,2,3-trimethyl-butane | 0 | 0.037 | 0.032 | 0.023 | 0.020 | 0.026 |
| 3,3-dimethyl-pentane | 0 | 0.019 | 0.014 | 0.010 | 0.009 | 0.012 |
| 2-methyl-hexane | 0 | 0.404 | 0.429 | 0.333 | 0.306 | 0.367 |
| 2,3-dimethyl-pentane | 0 | 0.145 | 0.151 | 0.116 | 0.105 | 0.127 |
| 3-methyl-hexane | 0 | 0.346 | 0.367 | 0.283 | 0.260 | 0.311 |
| 3-ethylpentane | 0 | 0.020 | 0.020 | 0.016 | 0.014 | 0.017 |
| Normal C$_7$ | 0 | 0.059 | 0.052 | 0.038 | 0.032 | 0.041 |
| 2,2-dimethyl-hexane | 0 | 0.014 | 0.012 | 0.009 | 0.008 | 0.010 |
| 2,5-dimethyl-hexane | 0 | 0.030 | 0.032 | 0.024 | 0.022 | 0.027 |
| 2,4-dimethyl-hexane | 0 | 0.033 | 0.035 | 0.027 | 0.024 | 0.030 |
| 3,3-dimethyl-hexane | 0 | 0.003 | 0.002 | 0.002 | 0.002 | 0.002 |
| 2,3-dimethyl-hexane | 0 | 0.012 | 0.013 | 0.010 | 0.009 | 0.011 |
| 2-methyl-heptane | 0 | 0.042 | 0.045 | 0.034 | 0.031 | 0.038 |
| 4-methyl-heptane | 0 | 0.014 | 0.015 | 0.011 | 0.010 | 0.013 |
| 3,4-dimethyl-hexane | 0 | 0.004 | 0.005 | 0.004 | 0.003 | 0.004 |
| 3-methyl-heptane | 0 | 0.042 | 0.045 | 0.034 | 0.031 | 0.038 |
| Unknown C$_8$ | 0 | 0.005 | 0.004 | 0.004 | 0.004 | 0.005 |
| C$_9^+$ | 0 | 0.112 | 0.123 | 0.117 | 0.118 | 0.131 |

As is evident from the results, the catalyst can still convert isopentane even after two reactivations.

EXAMPLE II

An 11 mL sample of a catalyst containing 18% gallium in a mixed (Ga/Al)$_2$O$_3$ support with 0.5% platinum was placed into a tubular reactor with an inert support above and below the catalyst. A nitrogen feed was set at 50 sccm and the temperature was set at 500° F. A 2.52 gram quantity of carbon tetrachloride was charged to the reactor at a rate of 0.035 mL/min. After this catalyst was chlorided, as described above, a pure isopentane feed was charged to the reactor at a feed rate of 22 mL/hr (LHSV=2 hr$^{-1}$). The initial pressure was set at 300 psig. Initial temperature was set at 235° F. and a hydrogen co-feed was set at 2.5 sccm. Table IV shows the results for five different samples taken approximately after 1, 2, 3, 4 and 5 hours on stream, respectively.

TABLE IV iC$_5$ Disproportionation Results from Platinum on Chlorided Alumina Catalyst with Gallium

| | Time On-Stream, Hours | | | | |
|---|---|---|---|---|---|
| | 1 Hour | 2 Hours | 3 Hours | 4 Hours | 5 Hours |
| | Total Product (wt %) | | | | |
| Propane | 0.03 | 0.01 | 0.01 | 0.00 | 0.00 |
| Isobutene | 14.18 | 5.27 | 5.13 | 2.63 | 1.64 |
| Isobutene | 0.00 | 0.00 | 0.00 | 0.00 | 0.00 |
| Normal Butane | 0.22 | 0.11 | 0.12 | 0.09 | 0.09 |
| Neo-pentane | 0.22 | 0.21 | 0.20 | 0.21 | 0.22 |
| Isopentane | 57.40 | 81.26 | 81.79 | 91.35 | 94.13 |
| Normal Pentane | 1.92 | 1.46 | 1.45 | 1.02 | 1.03 |
| Unknown C$_1$–C$_5$ | 0.05 | 0.04 | 0.03 | 0.02 | 0.02 |
| 2,2-dimethylbutane | 0.84 | 0.29 | 0.32 | 0.08 | 0.03 |
| 2,3-dimethylbutane | 2.27 | 1.14 | 1.03 | 0.45 | 0.28 |
| 2-methylpentane | 7.02 | 4.07 | 3.77 | 1.91 | 1.34 |
| 3-methylpentane | 3.17 | 1.86 | 1.80 | 0.93 | 0.67 |
| Normal Hexane | 0.38 | 0.14 | 0.14 | 0.05 | 0.03 |
| C$_7^+$ | 12.30 | 4.13 | 4.22 | 1.25 | 0.54 |
| Total C$_6^+$ | 25.98 | 11.63 | 11.28 | 4.66 | 2.88 |
| C$_6$ Selectivity | 52.7 | 64.5 | 62.5 | 73.3 | 81.2 |

As is evident from the results, the catalyst as prepared in Example II is also useful for converting isopentane.

The pressure was then decreased to 25 psig. The hydrogen co-feed was set at 5 sccm. Table V shows the results for three different samples taken after approximately 6 hours, 8 hours, and 10 hours on stream, respectively.

TABLE V i-C$_5$ Disproporationation Results from Platinum on Chlorided Alumina Catalyst with Gallium

| | Time on Stream Hours | | |
|---|---|---|---|
| | 6 Hours | 8 Hours | 10 Hours |
| | Liquid Product (wt %) | | |
| Propane | 0.001 | 0 | 0 |
| Isobutane | 0.356 | 0.257 | 0.285 |
| Normal Butane | 0.078 | 0.079 | 0.082 |
| Neo-pentane | 0.204 | 0.208 | 0.212 |
| Isopentane | 95.494 | 98.200 | 98.503 |
| Normal Pentane | 0.42 | 0.428 | 0.432 |
| 2,2-dimethylbutane | 0.001 | 0 | 0 |
| 2,3-dimethylbutane | 0.046 | 0.031 | 0.028 |
| 2-methylpentane | 0.308 | 0.233 | 0.224 |
| 3-methylpentane | 0.187 | 0.135 | 0.130 |
| Normal Hexane | 0.002 | 0.001 | 0.001 |
| C$_7^+$ | 2.902 | 0.429 | 0.103 |
| | Offgas (wt %) | | |
| Propane | 0.304 | 0.136 | 0.066 |
| Isobutane | 12.401 | 6.403 | 3.651 |
| Normal Butane | 0.292 | 0.243 | 0.232 |
| Neo-pentane | 0 | 0.332 | 0.377 |
| Isopentane | 72.047 | 83.163 | 90.403 |
| Normal Pentane | 1.075 | 0.529 | 0.400 |
| 2,2-dimethylbutane | 0 | 0.063 | 0.035 |
| 2,3-dimethylbutane | 0.616 | 0.254 | 0.125 |
| 2-methylpentane | 2.022 | 0.798 | 0.410 |
| 3-methylpentane | 1.095 | 0.352 | 0.190 |
| Normal Hexane | 0 | 0.068 | 0.034 |
| C$_7^+$ | 10.149 | 7.659 | 4.075 |
| | Combined (wt %) | | |
| Propane | 0.128 | 0.028 | 0.010 |
| Isobutane | 5.423 | 1.525 | 0.781 |
| Normal Butane | 0.168 | 0.113 | 0.104 |
| Neo-pentane | 0.118 | 0.234 | 0.236 |
| Isopentane | 85.630 | 95.098 | 97.309 |
| Normal Pentane | 0.696 | 0.448 | 0.427 |
| 2,2-dimethylbutane | 0.001 | 0.013 | 0.005 |
| 2,3-dimethylbutane | 0.286 | 0.077 | 0.042 |
| 2-methylpentane | 1.029 | 0.349 | 0.251 |
| 3-methylpentane | 0.569 | 0.179 | 0.139 |
| Normal Hexane | 0.001 | 0.015 | 0.006 |
| C$_7^+$ | 5.951 | 1.920 | 0.689 |
| Isopentane Conversion | 14.5% | 4.0% | 2.5% |

As is evident from Table V, the catalyst as prepared in Example II can also convert isopentane after being reactivated.

Whereas this invention has been described in terms of the preferred embodiments, reasonable variations and modifications are possible by those skilled in the art. Such modifications are within the scope of the described invention and appended claims.

That which is claimed:

1. A process for disproportionating hydrocarbons comprising contacting a hydrocarbon feed comprising at least one paraffin and an initiator selected from the group consisting of a chloroalkane, a branched paraffin, at least one olefin, and combinations of any two or more thereof, with a catalyst comprising:
   (a) a support component,
   (b) a metal selected from the group consisting of platinum, palladium, iron, cobalt, nickel, zinc, ruthenium, rhodium, osmium, iridium, and combinations of any two or more thereof, and
   (c) a halogen selected from the group consisting of chlorine, bromine, and combinations thereof; and
   (d) gallium;
in a disproportionation reaction zone under disproportionation reaction conditions; and reactivating said catalyst by stripping said catalyst with hydrogen.

2. A process in accordance with claim 1 wherein the concentration of said initiator in said disproportionation reaction zone, based on the combined weight of said hydrocarbon feed and said initiator in said reaction zone, is at least about 0.01 weight percent.

3. A process in accordance with claim 1 wherein the concentration of said initiator compound in said reaction zone, based on the combined weight of said hydrocarbon feed and said initiator in said reaction zone, is at least about 0.1 weight percent.

4. A process in accordance with claim 1 wherein the concentration of said initiator in said reaction zone, based on the combined weight of said hydrocarbon feed and said initiator in said reaction zone, is at least 0.9 weight percent.

5. A process in accordance with claim 1 wherein said at least one olefin has in the range of from 2 to 20 carbon atoms per molecule.

6. A process in accordance with claim 1 wherein said at least one olefin has in the range of from 3 to 8 carbon atoms per molecule.

7. A process in accordance with claim 1 wherein said at least one olefin has in the range of from 5 to 6 carbon atoms per molecule.

8. A process in accordance with claim 1 wherein said disproportionation reaction conditions include a temperature in the range of from about 75° F. to about 500° F.

9. A process in accordance with claim 1 wherein said disproportionation reaction conditions include a temperature in the range of from about 100° F. to about 300° F.

10. A process in accordance with claim 1 wherein said disproportionation reaction conditions include a temperature in the range of from 200° F. to 300° F.

11. A process in accordance with claim 1 wherein said metal of said catalyst is selected from the group consisting of platinum, palladium, and combinations thereof.

12. A process in accordance with claim 1 wherein said halogen of said catalyst is selected from the group consisting of chlorine, bromine and combinations thereof.

13. A process in accordance with claim 1 wherein said support component of said catalyst is selected from the group consisting of alumina, silica-alumina, a zeolite, zirconia, a borate, an aluminum borate, and combinations thereof.

14. A process in accordance with claim 1 wherein said metal of said catalyst comprises platinum, said halogen of said catalyst comprises chlorine, and said support component of said catalyst comprises alumina.

* * * * *